United States Patent [19]

Pereira

[11] Patent Number: 4,689,225

[45] Date of Patent: Aug. 25, 1987

[54] VACCINE FOR CYTOMEGALOVIRUS

[75] Inventor: Lenore Pereira, Berkeley, Calif.

[73] Assignee: Institut Merieux, Charbonnieres, France

[21] Appl. No.: 667,792

[22] Filed: Nov. 2, 1984

[51] Int. Cl.[4] ............................................. A61K 39/12
[52] U.S. Cl. ........................................ 424/89; 424/88; 435/235; 435/948
[58] Field of Search ................... 424/89; 435/235, 948

[56] References Cited

U.S. PATENT DOCUMENTS

| | | | |
|---|---|---|---|
| 3,959,466 | 5/1976 | Plotkin | 424/89 |
| 4,058,598 | 11/1977 | Stern et al. | 424/89 |
| 4,452,734 | 6/1984 | Larson et al. | 435/239 |

OTHER PUBLICATIONS

Pereira et al, "Polymorphism of Human Cytomegalovirus . . . MAB", *J. Virol.*, 139, 1984, pp. 73–86.
Pereira et al., *Infect. and Imm.*, vol. 36(3), 1982, pp. 924–942.
Stagno et al, "Congenital Cytomegalovirus Infection", *N. Eng. J. Med.*, vol. 296(22), 1979, pp. 1254–1258.
Starr et al, "Specific Cellular and Humarol Immunity after Immunization . . . Vaccine", *J. Inf. Dis.*, 143(4), 1981, pp. 585–589.
*Virology*, 2nd Ed., Joklik, 1985, pp. 207–210.
Pereira et al. (1983) Infection and Immunology 39:100–108.

*Primary Examiner*—Morton Foelak
*Assistant Examiner*—Garnette D. Draper
*Attorney, Agent, or Firm*—Bertram I. Rowland

[57] ABSTRACT

A novel subunit vaccine employing glycoprotein A of human cytomegalovirus or fragments thereof is provided. The vaccine is particularly suitable for inoculation of immunosuppressed individuals and women of childbearing age to inhibit the transmission of hCMV to the fetus.

8 Claims, No Drawings

VACCINE FOR CYTOMEGALOVIRUS

BACKGROUND OF THE INVENTION

1. Field of the Invention

Vaccination against both bacterial and viral diseases has been one of the major accomplishments of medicine over the past century. While effective vaccines have been developed for a large number of diseases, the development of safe and effective vaccines for a number of other diseases remains problematic. The use of killed microbial agents as vaccines, although generally safe, will not always be effective if the immunogenic characteristics of the agent are altered. In contrast, the preparation of live, attenuated microbial agents as vaccines will often provide improved immunologic reactivity, but will also increase the risk that the vaccine itself will be infectious, e.g., as a result of reversion, and that the organism will be able to propagate and provide a reservoir for future infection. Thus, although much experience has been gained over the years relating to the preparation of bacterial and viral vaccines, the successful preparation of an effective vaccine against a particular infectious agent can never be assured, even when employing techniques which have been successful for other infectious microorganisms.

Cytomegalovirus (CMV) infection is the leading cause of congenital viral infections, with an incidence averaging 1% of all live births. An additional 5% to 10% of infants acquire CMV perinatally, as a result of mother-to-infant transmission. Although the majority of infants with congenital and perinatal CMV infections are asymptomatic, the disease can be severe and even fatal, usually affecting the salivary glands, brain, kidneys, liver, and lungs. Latent infections by the virus may be subsequently activated by pregnancy, multiple blood transfusions, or immunosuppression for organ transplantation. For that reason, it would be desirable to provide a safe, effective and economic vaccine capable of affording protection against cytomegalovirus infections, particularly for women of child bearing age to avoid transmission of the disease to their children and for immunosuppressed individuals for whom CMV infection can be fatal.

2. Description of the Prior Art

Pereira et al. (1982) Infect. Immun. 36:924–932 describe the preparation of a panel of monoclonal antibodies specific for three antigenically distinct groups of cytomegalovirus glycoproteins, including glycoprotein A as the present invention. See also, Pereira et al. (1983) Infect. Immun. 39:100–108 which describes the electrophoretic properties of at least 11 polypeptides immune precipitated from sera of children infected by CMV infection.

SUMMARY OF THE INVENTION

The present invention provides a method and vaccine for conferring humoral immunity to cytomegalovirus (CMV) infection. The vaccine is a subunit vaccine incorporating polypeptides having immunological activity corresponding to that of glycoprotein A of the cytomegalovirus and being present in a physiologically-acceptable medium in an amount effective to elicit viral neutralizing activity in a human host.

DESCRIPTION OF THE SPECIFIC EMBODIMENTS

Polypeptides having immunological activity analogous to that of glycoprotein A (gA) of human cytomegalovirus (hCMV) are incorporated into vaccines and used to inoculate susceptible hosts to provide immunity against hCMV infection.

Human cytomegalovirus is a herpesvirus, and hCMV virions include a DNA core, an icosahedral capsid, a tegument or matrix, and an outer membrane designated as the envelope. The envelope includes at least four antigenically distinct glycoproteins as described by Pereira et al. (1982) supra. As described in the Experimental section hereinafter, the four glycoproteins are designated gA, gB, gC, and gD. Among each of these antigenically distinct classes of glycoprotein exist a number of different forms having differing degrees of glycosylation. The gA polypeptides may be identified by their susceptibility to endoglycosidase H digestion (as discussed in the Experimental section hereinafter) and by reaction with a gA-specific monoclonal antibody, such as CH-28-1, as described in the Experimental section hereinafter.

The present invention is based on the discovery that glycoprotein A (gA) is suitable for use as the immunological substance in a vaccine for conferring immunity against hCMV infection. Any of the naturally occurring forms of gA can be utilized in the vaccine, so long as the form is capable of eliciting viral neutralizing activity against hCMV in the inoculated host. Viral neutralizing activity is defined as the ability of antisera produced in response to immunization with the gA to inhibit hCMV multiplication in a plaque assay on a suitable cell culture. Generally, the plaque reduction in an assay as described in the Experimental section hereinafter resulting from contact with the antisera will be at least 50%, preferably at least 75%, more preferably 90% or greater.

As used hereinafter and in the claims, glycoprotein A (gA) of human cytomegalovirus (hCMV) will refer to a polypeptide product which displays immunological activity cross-reactive with natural glycoprotein A or fragments thereof as measured in recognized bioassays. Specifically, the gA polypeptide will be able to elicit antibodies displaying a neutralizing activity against hCMV when administered to a susceptible host. The gA polypeptide will have an amino acid sequence which is the same or substantially the same as the natural glycoprotein, usually differing by no more than 50 amino acids, more usually differing by 25 or fewer amino acids. For the most part, the gA amino acid sequence will differ, if at all, by substitutions among the non-polar amino acids, i.e., aliphatic and aromatic amino acids. The deviations from the natural amino acid sequence will not adversely affect the immunogenic activity of the polypeptide. The gA polypeptide may be obtained from a natural source, i.e., an hCMV-infected cell line, by suitable separation techniques, as described hereinbelow. Alternatively, the gA polypeptide may be produced by synthetic techniques, e.g., solid-phase synthesis (for immunogenic fragments of the polypeptide), or by expression of a gA gene in a suitable microorganism host by recombinant DNA techniques.

In addition to use of the entire gA polypeptide, immunogenic fragments of the gA polypeptide may also find use. Such shorter fragments will correspond to epitopic region(s) on the natural gA polypeptide, comprising at least nine amino acids, usually at least twelve amino acids, and preferably at least fifteen amino acids or more. When employing polypeptides below about 5 kD, it will usually be necesary to conjugate the gA fragment to an appropriate immunogenic carrier in order to elicit the desired immune response. Suitable immunogenic carriers include tetanus toxoid, hepatitus B surface antigen, and the like. Methods for conjugating such haptenic fragments to the carriers are well known in the art.

The gA polypeptide may be isolated and purified from its natural source as follows. A suitable hCMV strain, such as AD169, is used to infect suitable human cells such as human fetal diploid lung cells. After growing the infected cells from about 96 to 120 hours or more in a suitable medium, the cells may be separated from the medium, washed, and lysed in a suitable buffer. A suitable inhibitor should be added to prevent proteolytic degradation of the glycoprotein. The gA may then be separated from the lysate using an immunoaffinity column which is specific for the gA polypeptides. A specific method for such purification is set forth in the Experimental section hereinafter.

Alternatively, fragments of the gA polypeptide may be prepared by conventional solid-phase synthesis techniques, such as those described by Merrifield (1963) J. Amer. Chem. Soc. 85:2149–2156. Such solid-phase synthesis techniques are suitable for preparations of polypeptide fragments of up to 50 to 100 amino acids, or more. Generally, however, as the length of the polypeptide increases, the difficulty in the synthesis increases and the desirability of employing a solid-phase synthesis technique diminishes.

The gA polypeptides, either the entire polypeptide or fragments thereof, may also be produced by expression of a gA gene in a suitable microorganism host. The gA gene may be viral DNA, cDNA, synthetic DNA, or a combination thereof, e.g., synthetic DNA may be combined with the cDNA to complete the gA gene. Conveniently, the gA DNA sequence will be incorporated in an extrachromosomal element including a replication system recognized by a desired host, and translational and transcriptional regulatory control sequences which provide for the expression of the gA gene. The extrachromosomal element may include a number of other features, such as selectable markers, which facilitate manipulation of the extrachromosomal element.

After a suitable extrachromosomal element has been prepared, it can be used to transform an appropriate host, and the gA polypeptide expressed in that host recovered and purified for use in the vaccines of the present invention. Purification of the gA polypeptide may be accomplished in a variety of ways, including immunoaffinity chromatography, ion exchange chromatography, high performance liquid chromatography, and the like. It is desired that the gA be greater than 80% pure, preferably at least 90% pure, more preferably at least 95% pure.

The vaccines of the present invention will incorporate one or more of the gA forms, and may include other immunogenic substances as desired to provide immunity against other infectious agents. The gA polypeptides will normally be incorporated in a physiologically-acceptable medium, such as water, saline, phosphate buffered saline, and may be administered intravenously or intraarterially. Often, an adjuvant will be incorporated into the vaccine to provide for release of the gA over a prolonged period. Suitable adjuvants include various inorganic gels, such as alum, aluminum hydroxide, aluminum phosphate, and the like. The amount of gA polypeptide employed per dose will generally be in the range from about 0.5 to 150 µg in a liquid volume of about 0.25 to 2 ml. The vaccines may be administered repeatedly at from 2 to 4 week intervals, usually for a total of 2 to 4 times.

Inoculation with the vaccine of the present invention is particularly suitable for individuals about to undergo immunosuppression, such as those undergoing skin grafting or organ transplantation. Such individuals, if they lack immunity (antibodies), are at great risk to hCMV infection. The vaccine is also of great benefit to women of childbearing years, preferably at or before the early stages of pregnancy. The primary threat from cytomegalovirus infection arises from transmission or reactivation of CMV during the gestation period. Thus, if the infective cycle of hCMV can be inhibited by stimulation of the mother's immune system, the likelihood of infection of the infant can be reduced or eliminated.

The following results are offered by way of illustration, not by way of limitation.

EXPERIMENTAL

Materials and Methods

1. Cell culture, media, and virus.

Human fetal diploid lung (HFDL) cells were grown in fortified Eagle's minimal essential medium (MEM), containing twice the standard concentration of vitamins and amino acids, supplemented with 10% fetal bovine serum. Properties of CMV strain AD169 were described in Rowe et al. (1965) Proc. Soc. Exp. Biol. Med. 92:418–424.

2. Monoclonal antibodies:

Procedures used for selection and characterization of hybridomas producing monoclonal antibodies to CMV were described by Pereira et al. (1982) Infect. Immun. 39:100–108.

3. Infection and radioactive labelling of infected cells.

HFDL cell monolayers in 32 oz. bottles were infected with CMV strain AD169 at a multiplicity of infection of 5 to 10 plaque forming units (PFU) per cell at 37° C. CMV-infected cells were radiolabelled from 96 to 120 hr postinfection with [$^{35}$S]methionine (10 µC/ml) (sp. act. 1200 mCi/mmol) in medium containing 10% methionine and 1% dialyzed fetal calf serum to label the late viral proteins. CMV glycoproteins were labelled from 96 to 120 hr postinfection with [$^{14}$C(U)]-mannose (1 µCi/ml, 210 mCi/mmol) or [1-$^{14}$C]glucosamine (1 µCi/ml, 45–60 mCi/mmol) in medium containing one-quarter the amount of glucose.

4. Immune precipitation tests.

Radiolabelled antigen was mixed with mouse ascites-containing monoclonal antibodies (5 µl) and incubated at room temperature for 1 hr. To collect the immune precipitates, 5 mg of protein A-Sepharose (Sigma) coated with rabbit anti-mouse immunoglobulin G (Miles) was added and the mixture incubated for 1 hr with gentle agitation. To remove unreacted antigen, the beads were washed three to five times with PBS containing 1% Nonidet P-40 and 1% sodium deoxycholate.

5. Preparation of samples for electrophoresis.

Sonicates of radiolabelled cells or immune precipitates were denatured and solubilized by heating for 2 to 3 min. at 100° C. in disruption buffer containing 2% sodium dodecyl sulfate (SDS), 5% β-mercaptoethanol, and 0.05M Tris-hydrochloride (pH 7.0).

6. Denaturing-polyacrylamide gel electrophoresis.

Polyacrylamide gel electrophoresis was done in a discontinuous buffer system containing 0.1% SDS. The stacker and separation gels contained 3 and 9% acrylamide, respectively, cross-linked with N,N-diallytartardiamide (Bio-Rad, Richmond, California) as described previously (Pereira et al. (1982) supra). Gels were fixed in methanol and acetic acid, dried, and exposed to X-ray film. In instances where it was desirable to shorten the exposure time, electrophoretically separated proteins in polyacrylamide gels were immobilized on the surface of nitrocellulose (as described below) and autoradiographed. Proteins used for calibration of molecular weights were myosin (220,000), β-galactosidase (130,000), phosphorylase B (94,000), bovine serum albumin (68,000), and ovalbumin (43,000) (Sigma Chemical Co.).

7. Purification of CMV glycoprotein A.

To prepare an immunoaffinity column, immunoglobulin CH28-1 (monoclonal antibody specific for gA but not gB, gC, or gD) was precipitated from mouse ascites with 50% saturated ammonium sulfate solution. The immunoglobulins were coupled to cyanogen bromide-activated Sepharose 4B (Sigma) as directed by the manufacturer and CMV glycoproteins purified as described previously for herpes simplex virus glycoproteins by Eisenberg et al. (1982) J. Virol. 41:1099–1104. Procedures for purification of gA were modified as follows: $4 \times 10^8$ infected HFDL cells were radiolabelled from 96 to 120 hr postinfection with [$^{35}$S]methionine (50 μC/ml) (sp. act. 1200 mCi/mmol) in medium containing 10% methionine or with [1-$^{14}$C]glucosamine (1 μCi/ml, 45-60 mCi/mmol) in medium containing one-quarter the amount of glucose. Cytoplasmic extracts were prepared with 1.0% NP-40 and 1.0% sodium deoxycholate in PBS containing $10^{-5}$M N-tolylsulfonyl L-phenylalanyl chloromethyl ketone and N-α-tosyl-L-lysine chloromethyl ketone to inhibit proteolytic activity. The nuclei were removed by centrifugation at 1200 rpm for 10 min. Extracts were centrifuged at 24,000 rpm in an SW41 rotor for 1 hr at 4° C. to remove insoluble proteins. Clarified extracts were first passed over a control immunoglobulin affinity column, then cycled over the specific column three times. The gA was eluted with 3M KSCN, concentrated, and dialyzed as reported previously.

To purify large amounts of gA for immunization, CMV infected cells ($4 \times 10^9$) were harvested when the viral induced cytopathic effect was complete, approximately 7 to 10 days post infection. Infected cells were extracted in non-ionic detergents and adsorbed to an immunoaffinity column as described above.

8. Endoglycosidase H digestion.

CMV infected cells were labelled with [$^{35}$S]methionine (100 μC/ml) from 96 to 120 hrs postinfection. gA was immune precipitated from extracts of infected cells with monoclonal antibodies. The immobilized glycoprotein was washed in PBS containing 1.0% NP40 detergent followed by 2 washes in PBS without the detergent. Duplicate samples of precipitates were resuspended in 100 μl of sodium citrate buffer (100 mM, pH 5.0). To one set of samples, 5 μl of 0.5 U/ml endoglycosidase H (endo H) (Boehringer Mannheim Biochemicals) was added and the samples were incubated at 37° C. After 1.5 hrs, a second 5 μl aliquot of enzyme was added and the samples incubated for 2 additional hrs. Samples were solubilized in disruption buffer, boiled, and electrophoresed in SDS-polyacrylamide gels, as described above.

RESULTS

1. Identification of four antigenically distinct glycoproteins in CMV-infected cells The following scheme was used to name the antigenically distinct glycoproteins in CMV-infected cells. Glycoproteins (g) precipitated by different monoclonal antibodies (i.e., immunologically distinct glycoproteins) were given the following letter designations: gA, gB, gC, or gD. Electrophoretically distinct forms with shared antigenic determinants were assigned numbers in order of decreasing apparent molecular weight, e.g., gA1, gA2, gA3 or gD1, gD2, etc. Electrophoretically separated glycoproteins immune precipitated from extracts of [$^{35}$S]methionine-labelled infected cells by monoclonal antibodies CH28-2, CH65-1, and CH16-1 represent three antigenically distinct glycoproteins designated as gA, gC, and gD. Profiles of methionine-labelled gB precipitated by monoclonal antibody CH33-1 were too weak to detect using [$^{35}$S]methionine labelled polypeptides, but were detected when radiolabelled with glucosamine.

Immune precipitates of CMV glycoproteins labelled with [$^{14}$C]mannose or [$^{14}$C]-glucosamine were electrophoretically separated in SDS-polyacrylamide gels. The results showed the following. (i) Analysis of gA showed that the closely migrating gA2 and gA3 bands were heavily labelled with mannose whereas gA1, gA4, and gA6 contained trace amounts. All members of the gA family labelled heavily with glucosamine. (ii) Trace amounts of mannose and glucosamine were incorporated into gB, gC1, gD1, and gD4. The characteristics of the various glycoproteins are set forth in Table 1.

TABLE 1

| Characteristics of CMV Glycoproteins | | |
|---|---|---|
| Form | Apparent MW ($\times 10^3$) | Properties |
| gA1 | 160–148 | Contains mannose and glucosamine, appears after 60-min chase |
| gA2 | 142 | Contains mannose and glucosamine, made during 15-min pulse, endo H sensitive |
| gA3 | 138 | Contains mannose and glucosamine, made during 15-min pulse, endo H sensitive, denatured in the presence of β-mercaptoethanol |
| gA4 | 123–107 | Accumulates in the presence of deoxyglycose, appears after a chase, contains mannose and glucosamine |
| gA5 | 95 | Accumulates in the presence of tunicamycin, an unglycosylated precursor |
| gA6 | 58.5 | Present after 60-min chase, contains mannose and glucosamine, endo H sensitive |
| gA7 | 56.5 | Accumulates in the presence of deoxyglucose |
| gB1 | 123–116 | Contains glucosamine and trace amounts of mannose |
| gB2 | 80 | Appears after a pulse |
| gC1 | 66 | Contains mannose and glucosamine |
| gC2 | 55 | " |
| gC3 | 50 | " |
| gC4 | 46 | " |
| gD1 | 49 | Contains mannose and glucosamine |
| gD2 | 48 | Contains mannose |
| gD3 | 34 | Contains mannose |
| gD4 | 25 | Contains mannose and glucosamine |

2. Monoclonal antibodies to gA

To further analyze the synthesis and processing of the gA glycoproteins, a panel of 30 monoclonal antibodies which immune precipitated this family of polymorphic glycoproteins was assembled. All but one of the antibodies to gA precipitated trace amounts of a band 160,000 to 148,000 in apparent molecular weight (gA1). A doublet comprised of polypeptides approximately 142,000 and 138,000 in apparent molecular weight (gA2 and gA3) was detected. In addition, trace amounts of a broad band 123,000 to 107,000 in apparent molecular weight (gA4) and a faster migrating band approximately 58,500 in apparent molecular weight (gA6) were precipitated. The exception was a monoclonal antibody which precipitated gA6 only.

Members of a panel of 16 monoclonal antibodies were divided into three major groups on the basis of (i) surface membrane immunofluorescence; (ii) neutralizing activity; and (iii) reactivity with electrophoretically separated, denatured polypeptides immobilized on nitrocellulose. Pereira et al. (1982) supra. The first group (I) reacted with a domain exposed on the surface membrane of intact CMV-infected cells. In the presence of SDS, these antibodies reacted with gA2-gA3 bands but not with gA6. The second group (II) had neutralizing activity but failed to react with denatured gA. The third group (III) was comprised of antibodies which retained reactivity with SDS-denatured gA but failed to neutralize virus or to react with domains exposed on the cell surface. These results are summarized in Table 2. Additional studies utilizing limited proteolysis of gA indicated that antibodies within groups reacted with different antigenic domains.

or tunicamycin, to allow rapidly processed, immature forms to accumulate. Infected cells treated with inhibitors were labelled for 24 hr. with [$^{35}$S]methionine, extracted, and reacted with monoclonal antibodies. The immune precipitates formed were solubilized and subjected to electrophoresis in SDS-polyacrylamide gels. The following are the results.

(i) Precipitates of cells treated with deoxyglucose contained large amounts of gA4, gA6, and a faster migrating band approximately 56,500 in apparent molecular weight, designated as gA7. It is notable that gA1, gA2, and gA3 were not precipitated from deoxyglucose-treated cells. The results suggested that gA4 and gA7, detected weakly or not at all in untreated cells, may be partially glycosylated intermediates which are rapidly processed.

(ii) All immune precipitates of tunicamycin-treated infected cells contained one weak band, approximately 95,000 in apparent molecular weight which we designated as gA5. The data suggested that this polypeptide is most likely the unglycosylated precursor of higher-molecular-weight forms.

4. Endoglycosidase H digestion of gA

In order to indentify forms of gA containing high-mannose oligosaccharides found in partially glycosylated precursors, the glycoprotein was immune precipitated from extracts of infected cells labelled for 24 hrs with [$^{35}$S]methionine, digested with endo H and subjected to electrophoresis in SDS-polyacrylamide gels. Analysis of autoradiograms comparing the electrophoretic mobility of immune precipitates obtained with monoclonal antibodies CH28-2 subjected to digestion with the enzyme and untreated samples are as follows.

TABLE 2

Properties of Monoclonal Antibodies to CMV Glycoprotein A (gA)

| Group | Mabs | RIP[a] | Immune[b] Transfer gA2-3, | gA6 | NT[c] −C' | +C' | Cell Surface Reactive[d] IF | BP | Ig |
|---|---|---|---|---|---|---|---|---|---|
| I | CH45-1 | + | + | − | + | + | + | + | G1 |
|  | CH86-3 | + | + | − | + | + | + | + | G1 |
| II | CH87-1 | + | − | − | + | + | − | + | G2a |
|  | CH92-1 | + | − | − | + | + | − | + | G2a |
|  | CH130-9 | + | − | − | + | + | − | + | G2a |
|  | CH244-4 | + | − | − | − | + | − | + | G1 |
|  | CH51-4 | + | − | − | − | + | − | + | G2b |
|  | CH114-5 | + | − | − | + | + | − | + | G2b |
|  | CH105-7 | + | − | − | − | + | − | + | G2a |
|  | CH112-1 | + | − | − | + | + | − | + | G1 |
|  | CH143-13 | + | − | − | − | + | − | + | G1 |
|  | CH177-3 | + | − | − | + | + | − | + | G2a |
|  | CH253-1 | + | − | − | + | + | − | + | G2a |
| III | CH28-2 | + | + | + | − | − | − | − | G1 |
|  | CH158-5 | + | + | + | − | − | ND | ND | M |
|  | CH216-2 | + | + | + | − | − | − | − | G1 |

[a]Radioimmune precipitation.
[b]Immune reaction of monoclonal antibodies with electrophoretically separated glycoproteins denatured with sodium dodecyl sulfate and mercaptoethanol and immobilized on nitrocellulose.
[c]Neutralizing Activity (50% plaques neutralized) with complement (+C') and without complement (−C').
[d]Cell surface reactive by immunofluorescence (IF) or biotin-avidin enhanced surface immunoassay, black plaque (BP).

3. Characterization of the partially glycosylated forms of gA

On the basis of shared reactivity with monoclonal antibodies, multiple polypeptide bands immune precipitated could be identified as antigenically related, partially glycosylated forms of gA undergoing processing-linked shifts in electrophoretic mobility. To identify glycoprotein precursors, CMV-infected cells were treated with inhibitors of glycosylation, deoxyglucose Profiles of undigested samples contained gA1, gA2-gA3, and gA6. After endo H digestion, the electrophoretic mobility of gA2-gA3 and gA6 was altered and two new bands with apparent molecular weights of 115,000 and 55,000 appeared. The data suggested that gA2, gA3, and gA6 contain high mannose oligosaccharide side chains which are cleaved by endo H. The electrophoretic properties of the novel forms generated by cleavage closely approximate those of gA4 and gA7 which accumulate after treating infected cells with deoxyglucose. The observation that the electrophoretic mobility of gA1 was not altered after enzymatic digestion suggested that this form was resistant to endo H cleavage and may contain complex oligosaccharides found in more fully processed glycoproteins.

5. Immunization of mice with purified glycoprotein A and determination of antisera activity (a) Immunization Protocol Set 1: Four adult BALB/c mice were injected with 250 μl of aluminum potassium sulfate (alum) precipitated purified glycoprotein A. Four additional injections spaced at two to three week intervals were given. Mice were bled two weeks after the second inoculation and all subsequent ones.

Set 2: Four adult BALB/c mice were injected with 250 μl of purified glycoprotein A in complete Freund's adjuvant. Three additional injections (200 μl of purified glycoprotein each) were given at two week intervals. Mice were bled 2 to 3 weeks after the second injection and last injection.

Set 3: Four adult BALB/c mice were injected with 400 μl of purified gA glycoprotein bound to monoclonal antibody CH28-2 linked to protein A Sepharose. Five additional injections of 400 μl of purified gA bound to sepharose were given at two to three week intervals. Mice were bled after the second immunization and all subsequent ones.

(b) Tests Done on Hyperimmune Sera from gA Immunized Mice

Mice were bled as described above, and sera were tested by (1) immunofluorescence on CMV infected cells, (2) immunoprecipitation of gA from nonionic detergent extracts of CMV infected cells, (3) immune reaction against SDS-denatured, electrophoretically separated gA immobilized on nitrocellulose (Western blots), and (4) plaque reduction assay for neutralizing activity against CMV strain AD169. Results of immunofluorescence tests were positive for each set of immunizations after the second injection of antigen. Tests 2, 3, and 4 became positive in each set of immunizations after the fourth injection. CMV plaque reduction assays were done as described by Schmidt et al. (1976) J. Clin. Micro. 4:61–66. The endpoint dilution of hyperimmune sera from mice immunized with purified gA which retained 50 percent neutralizing activity agarnst approximately 100 plaque forming units was 1:100.

(c) Production of Monoclonal Antibodies from gA Immunized Mice

Spleens from two mice immunized with gA were used for somatic cell fusions to produce hybridomas secreting monoclonal antibodies. These fusions produced monoclonal antibodies to gA only.

(d) Immune Reaction of Patient Sera with Purified Glycoprotein A

Nine patient sera were reacted with electrophoretically separated gA immobilized on nitrocellulose. The sera had highly variable titers by complement fixation tests with CMV antigens and showed some reaction with CMV polypeptides by immunoprecipitation tests. For this procedure, patient sera were reacted with SDS-denatured, immobilized glycoprotein A, followed by binding of horseradish peroxidase-coupled rabbit anti-human immunoglobulin, and exposed to 4-chloro-1-naphthol and hydrogen peroxide to develop the colored substrate. Four of nine sera reacted with electrophoretically separated bands gA2-gA3 and gA6-gA7. Of these, one serum also reacted with gA1 and gA4.

According to the present invention, a novel vaccine employing glycoprotein A of hCMV or fragments thereof as the immunogenic substance is provided. The vaccine is particularly suitable for inoculation of expectant mothers to reduce the likelihood of severe primary CMV infection and transmission of hCMV infection to the fetus and for organ transplant recipients and individuals who will receive immunosuppressive drugs.

Although the foregoing invention has been described in detail for purposes of clarity of understanding, it will be obvious that certain changes and modifications may be practiced within the scope of the appended claims.

What is claimed is:

1. A method for vaccinating a susceptible host to confer humoral immunity to human cytomegalovirus (hCMV), said method comprising inoculating the host with a polypeptide having immunological activity cross-reactive with that of glycoprotein A of cytomegalovirus and having substantially the same sequence as naturally-occurring glycoprotein A, said polypeptide being present in a physiologically-acceptable carrier in an amount effective to elicit viral neutralizing activity against the cytomegalovirus.

2. A method as in claim 1, wherein the glycoprotein A is isolated from hCMV-infected cells.

3. A method as in claim 1, wherein the glycoprotein A is isolated by extraction in a non-ionic detergent followed by adsorption in an immunoaffinity column.

4. A method as in claim 1, wherein the glycoprotein A is a mixture of different antigenically related forms having varying amounts of glycosylation and different electrophoretic properties.

5. A vaccine against human cytomegalovirus (hCMV) infection, said vaccine comprising a polypeptide having immunological activity cross-reactive with glycoprotein A of the cytomegalovirus and having substantially the same sequence as naturally-occurring glycoprotein A, said polypeptide being present in an immunologically acceptable carrier in an amount effective to elicit viral neutralizing activity against cytomegalovirus when administered to a susceptible host.

6. A vaccine as in claim 5, wherein the glycoprotein A is isolated from hCMV-infected cells.

7. A vaccine as in claim 6, wherein the glycoprotein A is isolated by extraction in a non-ionic detergent followed by adsorption to an affinity column.

8. A vaccine as in claim 5, wherein the glycoprotein A is a mixture of different antigenically related forms having varying amounts of glycosylation and different electrophoretic properties.

* * * * *